United States Patent
Dekker et al.

(10) Patent No.: US 9,730,636 B2
(45) Date of Patent: Aug. 15, 2017

(54) MINIMALLY INVASIVE MEDICAL INSTRUMENT

(71) Applicant: KONINKLIJKE PHILIPS N.V., Eindhoven (NL)

(72) Inventors: Ronald Dekker, Eindhoven (NL); Vincent Adrianus Henneken, Eindhoven (NL); Antonia Cornelia Van Rens, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 126 days.

(21) Appl. No.: 14/410,621

(22) PCT Filed: Jun. 25, 2013

(86) PCT No.: PCT/IB2013/055199
§ 371 (c)(1),
(2) Date: Dec. 23, 2014

(87) PCT Pub. No.: WO2014/006536
PCT Pub. Date: Jan. 9, 2014

(65) Prior Publication Data
US 2015/0342530 A1    Dec. 3, 2015

Related U.S. Application Data

(60) Provisional application No. 61/666,958, filed on Jul. 2, 2012.

(51) Int. Cl.
*A61B 5/05* (2006.01)
*A61B 5/00* (2006.01)
(Continued)

(52) U.S. Cl.
CPC .......... *A61B 5/6847* (2013.01); *A61B 1/0011* (2013.01); *A61B 1/00013* (2013.01);
(Continued)

(58) Field of Classification Search
CPC ........... A61B 5/06; A61B 1/045; A61B 1/051; A61B 1/07; A61B 5/0017; A61B 1/00126; A61B 1/00013
See application file for complete search history.

(56) References Cited

U.S. PATENT DOCUMENTS 5,377,388 A    1/1995  De Bever
6,485,413 B1 *  11/2002  Boppart .............. A61B 1/00096
                                                    356/450
(Continued)

FOREIGN PATENT DOCUMENTS

CN    101563019 A    10/2009
JP    09122121 A    5/1997
(Continued)

OTHER PUBLICATIONS

"A Novel Ultra-Flexible Technology for Smart Invasive Medical Instruments". Minoun et al, Stretchable Electronics and Conformal Biointerfaces, vol. 1271E, JJ-05-09 , 2010.
(Continued)

*Primary Examiner* — Joel Lamprecht

(57) ABSTRACT

The present invention relates to a minimally invasive medical instrument (100) having a proximal end (100*b*) and a distal end (100*a*) and comprising a sensor arrangement (10) arranged at the distal end (100*b*) of the medical instrument (100). The sensor arrangement (10) comprises a sensor (20) configured to generate sensor data in the form of an electrical sensor signal, and a data conversion device (40) configured to convert the electrical sensor signal into an optical signal and comprising an electrical input (41) for receiving the electrical sensor signal and an optical output (42) for transmitting the optical signal. The sensor arrangement (10) further comprises an optical fiber (50) configured to transmit the optical signal from the distal end (100*a*) to the proximal end (100*b*), the optical fiber (50) coupled to the
(Continued)

output of the data conversion device (40) for receiving the optical signal, the optical fiber (50) extending from the distal end (100a) to the proximal end (100b) of the instrument (100). The present invention further relates to a method of manufacturing such a minimally invasive medical instrument (100).

15 Claims, 10 Drawing Sheets

(51) Int. Cl.
  A61B 1/06 (2006.01)
  A61B 1/07 (2006.01)
  A61B 1/00 (2006.01)
  A61B 1/05 (2006.01)
  A61B 8/12 (2006.01)
  G02B 6/42 (2006.01)
  A61B 90/00 (2016.01)
  A61B 17/00 (2006.01)
  A61B 17/22 (2006.01)
  A61B 5/0215 (2006.01)

(52) U.S. Cl.
  CPC ............. *A61B 1/051* (2013.01); *A61B 1/063* (2013.01); *A61B 1/0684* (2013.01); *A61B 1/07* (2013.01); *A61B 5/0084* (2013.01); *A61B 5/6851* (2013.01); *A61B 5/6852* (2013.01); *A61B 5/7278* (2013.01); *A61B 8/12* (2013.01); *A61B 17/00234* (2013.01); *A61B 90/361* (2016.02); *G02B 6/4202* (2013.01); *A61B 5/0017* (2013.01); *A61B 5/0215* (2013.01); *A61B 2017/00022* (2013.01); *A61B 2017/00296* (2013.01); *A61B 2017/00911* (2013.01); *A61B 2017/22042* (2013.01); *A61B 2090/3784* (2016.02); *A61B 2562/228* (2013.01); *G02B 6/4239* (2013.01); *Y10T 29/49171* (2015.01)

(56) References Cited

U.S. PATENT DOCUMENTS

| | | | |
|---|---|---|---|
| 6,952,530 B2 | 10/2005 | Helvajian | |
| 9,107,574 B2 | 8/2015 | Goldfarb et al. | |
| 2003/0021551 A1 | 1/2003 | Carpender | |
| 2006/0036164 A1* | 2/2006 | Wilson | A61B 5/06 600/424 |
| 2007/0232860 A1 | 10/2007 | Kubo et al. | |
| 2007/0286231 A1 | 12/2007 | Kubo et al. | |
| 2011/0144502 A1 | 6/2011 | Zhou et al. | |
| 2013/0182099 A1* | 7/2013 | Nakamura | A61B 1/00126 348/86 |
| 2013/0317372 A1* | 11/2013 | Eberle | A61B 5/02154 600/478 |

FOREIGN PATENT DOCUMENTS

| | | |
|---|---|---|
| JP | 2003210461 A | 7/2003 |
| JP | 2012069882 | 4/2012 |
| WO | 2012037377 A2 | 3/2012 |
| WO | 2012043187 A1 | 4/2012 |

OTHER PUBLICATIONS

"Fractional Flow Reserve Versus Angiography for Guiding Percutaneous . . . " Tonino et al, New England Journal of Medicine Jan. 15, 2009, vol. 360, No. 3 p. 213-224.

* cited by examiner

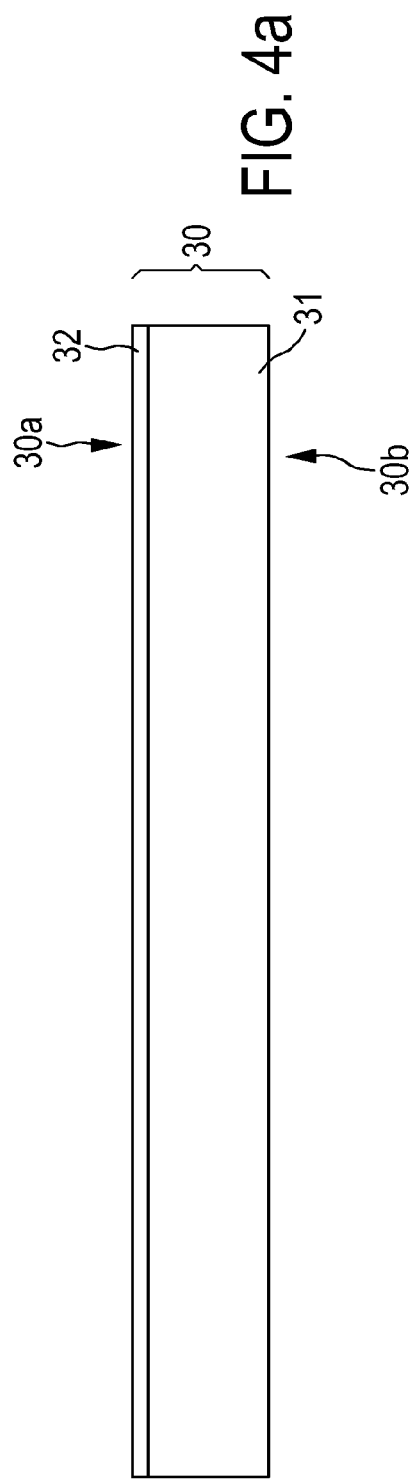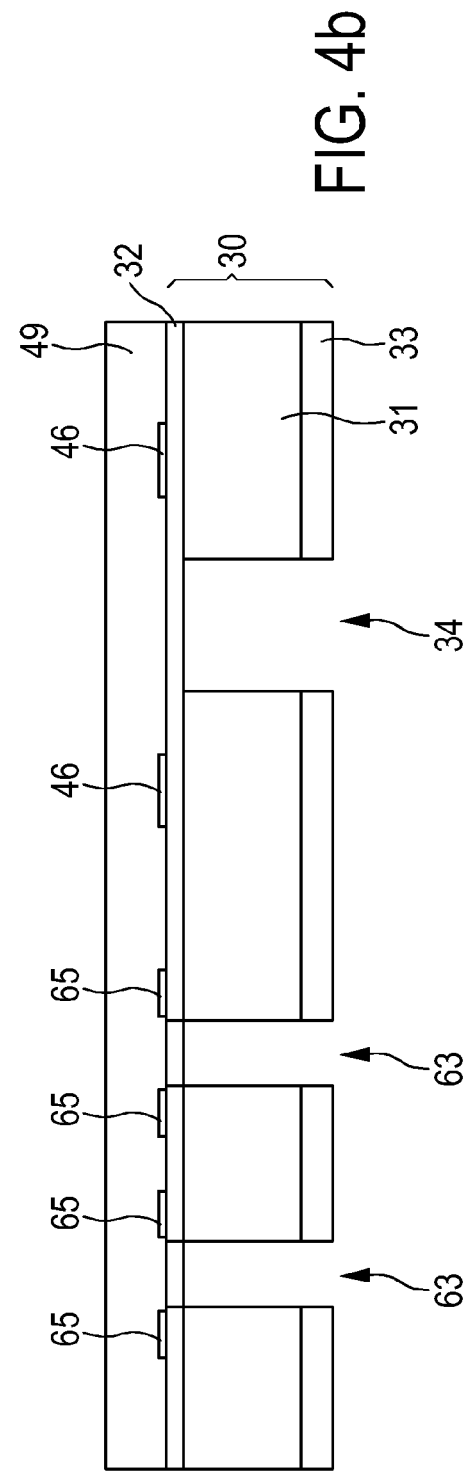

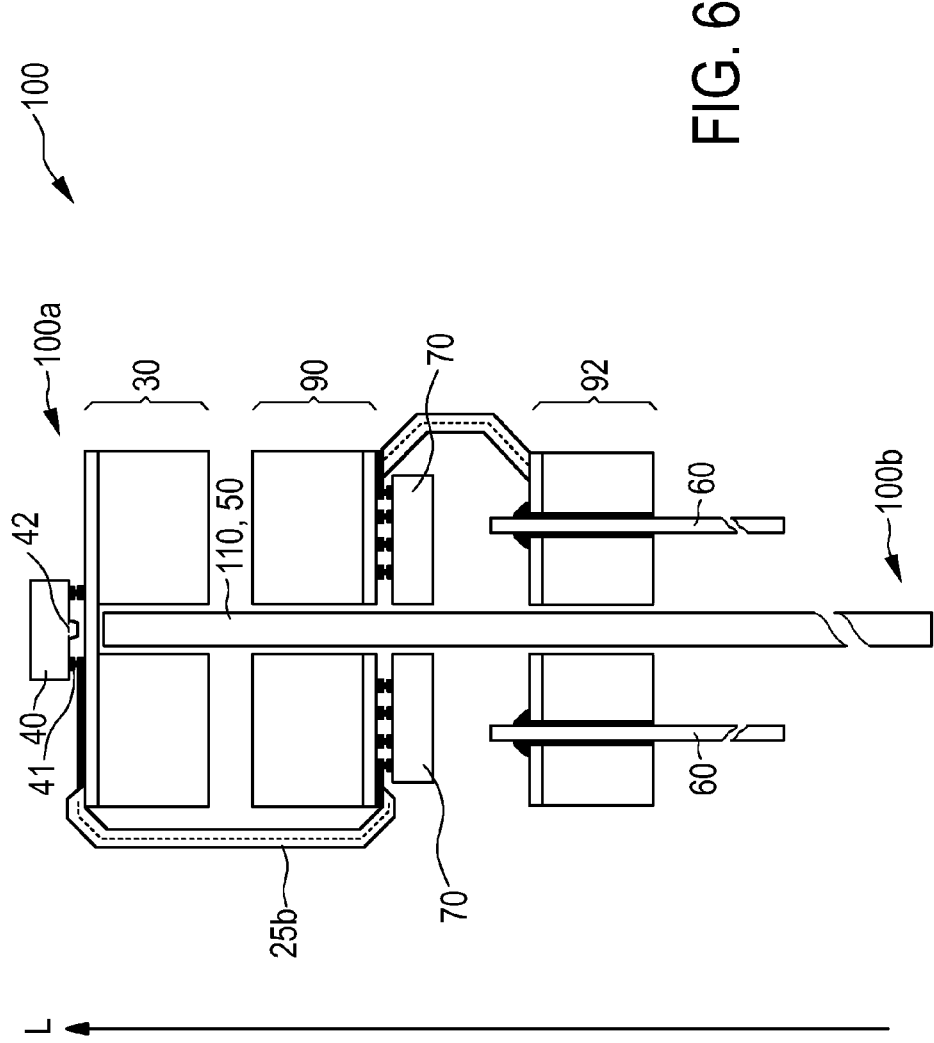

MINIMALLY INVASIVE MEDICAL INSTRUMENT

This application is the U.S. National Phase application under 35 U.S.C. §371 of International Application No. PCT/IB2013/055199, filed on Jun. 25, 2013, which claims the benefit of U.S. Provisional Application No.61/666,958 filed on Jul. 2, 2012. These applications are hereby incorporated by reference herein.

FIELD OF THE INVENTION

The present invention relates to a minimally invasive medical instrument having a proximal end and a distal end and comprising a sensor arrangement arranged at the distal end of the medical instrument. The sensor arrangement comprises a sensor configured to generate sensor data in form of an electrical sensor signal, in particular a medical imaging sensor, such as for example an ultrasound transducer or a camera. The present invention further relates to a method for manufacturing such a minimally invasive medical instrument. The present invention further relates to such a sensor arrangement and method of manufacturing such a sensor arrangement.

BACKGROUND OF THE INVENTION

There is a trend to integrate electronic functionality in the form of intelligent sensors at the tip of a minimally invasive medical instrument. These sensors can help the physician to guide the medical instrument through the body, or can allow for a more accurate diagnosis. For example, the use of a sensor, such as an optical camera or ultrasound transducer, is well-known at the tip of an endoscope. However, such electronic functionality is also envisioned for smaller medical instruments, such as catheters or (catheter) guide wires.

For example, the paper "Flex-to-Rigid (F2R): A Novel Ultra-Flexible Technology for Smart Invasive Medical Instruments", Benjamin Mimoun, Vincent Henneken, Ronald Dekker, published in "Stretchable Electronics and Conformal Biointerfaces (Mater. Res. Soc. Symp. Proc. Volume 1271E, Warrendale, Pa., 2010), paper 1271-JJ05-09" (see also ectm.ewi.tudelft.nl/linkto/ectm_publications.php), which is incorporated by reference herein, discloses a technology for the fabrication of partially flexible miniature sensors interconnected by ultra-flexible interconnects, in particular for use in a smart or minimally invasive medical instrument.

Given the small size of such a sensor or sensor arrangement, generally no data compression hardware can be included at the distal tip of the medical instrument. Therefore, a relatively high data rate of sensor data, for example from an ultrasound transducer or camera, is generated. For a high data rate, generally an electrical wire with a well defined characteristic impedance is required, such as a coaxial cable. However, the smallest coaxial cable has a diameter of several hundreds of µm. For example only a single coaxial cable may fit in a minimally invasive medical instrument (e.g. a guide wire having a 300 µm diameter), which limits the data rate. Thus, a high data rate has so far required the use of electrical wires, extending from the distal end to the proximal end of the medical instrument, which require a lot of space. The use of such wires requiring a lot of space, however, makes the medical instrument larger which is not desirable, in particular for a minimally invasive medical instrument. Therefore, so far a tradeoff between the data rate and the size of the medical instrument had to be made.

SUMMARY OF THE INVENTION

It is an object of the present invention to provide an improved minimally invasive medical instrument and method of manufacturing the same, in particular a minimally invasive medical instrument that enables the transmission of sensor data at a high data rate from the distal end to the proximal end of the instrument, while still providing a small sized medical instrument.

In a first aspect of the present invention, a minimally invasive medical instrument is presented having a proximal end and a distal end and comprising a sensor arrangement arranged at the distal end of the medical instrument, the sensor arrangement comprising a sensor configured to generate sensor data in the form of an electrical sensor signal. The sensor arrangement further comprises a data conversion device configured to convert the electrical sensor signal into an optical signal and comprising an electrical input for receiving the electrical sensor signal and an optical output for transmitting the optical signal. The sensor arrangement further comprises an optical fiber configured to transmit the optical signal from the distal end to the proximal end, the optical fiber coupled to the output of the data conversion device for receiving the optical signal, the optical fiber extending from the distal end to the proximal end of the instrument.

In a further aspect of the present invention a method for manufacturing a minimally invasive medical instrument having a proximal end and a distal end is presented, the method comprising manufacturing a sensor arrangement comprising: providing a sensor configured to generate sensor data in the form of an electrical sensor signal, providing a data conversion device configured to convert the electrical sensor signal into an optical signal and comprising an electrical input for receiving the electrical sensor signal and an optical output for transmitting the optical signal, providing an optical fiber configured to transmit the optical signal from the distal end to the proximal end, and coupling the optical fiber to the output of the data conversion device for receiving the optical signal. The method further comprises arranging the sensor arrangement at the distal end of the medical instrument, the optical fiber extending from the distal end to the proximal end of the instrument.

In a further aspect of the present invention such a sensor arrangement is presented. In yet a further aspect of the present invention a method of manufacturing such a sensor arrangement is presented.

The basic idea of the invention is to use an optical fiber for transmitting the high-data-rate sensor data from the distal end to the proximal end of the medical instrument. This provides a high-speed optical data link from the distal end or tip of the medical instrument. Given the small size of the minimally invasive medical instrument, no data compression hardware can be included at the distal end, and thus a relatively high data rate is generated at the distal end and transmitted via the optical data link to the proximal end of the device. In order to convert the electrical sensor signal generated by the sensor into an optical signal that can be transmitted by the optical fiber, a data conversion device is used. In particular, the optical fiber has a first end and a second end, wherein the first end is coupled to the optical output of the data conversion device and the second end is arranged at the proximal end of the device, for example connecting to a signal processing device. In this way a minimally invasive device that enables the transmission of sensor data at a high data rate, while still providing a small sized medical instrument, is provided. Furthermore, by using an optical fiber instead of an electrical wire, the signal is electrically isolated. This makes the medical device more MRI compatible and/or reduces noise (e.g. through ground loops or RFI (Radio Frequency Interference)).

In one example, the sensor can be a medical imaging sensor. A medical imaging sensor can generate sensor data representing an image (e.g. of the patient's body or part thereof). A medical imaging sensor can generate a high amount of sensor data, thus a high data rate, which requires a high data rate transmission. In one example, the sensor can be an ultrasound transducer configured to transmit and/or receive ultrasound waves, in particular a capacitive micromachined ultrasound transducer (CMUT). In another example, the sensor can be a camera. These are particularly useful sensors for medical imaging. However, it will be understood that in general any other type of sensor can be used, in particular a sensor generating a high data rate.

Preferred embodiments of the invention are defined in the dependent claims. It shall be understood that the claimed method of manufacturing a minimally invasive medical instrument has similar and/or identical preferred embodiments as the claimed medical instrument and as defined in the dependent claims. Further, it shall be understood that the sensor arrangement or method of manufacturing the sensor arrangement has similar and/or identical preferred embodiments as the claimed medical instrument or method of manufacturing the same.

In one embodiment, the sensor arrangement further comprises a substrate having a first surface and a second surface, the data conversion device arranged on the first substrate surface. In this way, a good support for the data conversion device is provided. In the corresponding method, the manufacturing of the sensor arrangement further comprises providing a substrate having a first surface and a second surface, and arranging the data conversion device on the first substrate surface.

In another embodiment or variant, the optical fiber is arranged in a hole in the substrate, the hole extending from the second substrate surface towards the first substrate surface. In this way, an easy way of coupling the optical fiber to the data conversion device is provided. In particular, the hole can be arranged perpendicular to the substrate surface(s). In this way, the optical fiber can be arranged perpendicular to the substrate surface(s). In particular, the hole can be arranged such that the first end of the optical fiber is coupled to the output of the data conversion device. For example, the data conversion device can be arranged to transmit the optical signal towards the first substrate surface, more particularly in a region where the first end of the optical fiber is located. In the corresponding method, the manufacturing of the sensor arrangement further comprises providing a hole in the substrate (e.g. by etching), the hole extending from the second substrate surface towards the first substrate surface, and arranging the optical fiber in the hole.

In a further embodiment or variant, the substrate has a base layer and at least one isolating layer on the base layer, the isolating layer forming at least the first substrate surface. In this way, by using an isolating layer, electrical connection(s) or electrical connection part(s) on the first substrate surface can be made, even if the base layer is conductive or semi-conductive. In particular, the substrate base layer can be made of silicon and/or the isolating layer can be made of silicon oxide. Using silicon is easy in manufacturing and/or cheap. In the corresponding method, providing the substrate comprises providing a base layer and providing at least one isolating layer on the base layer, the isolating layer forming at least the first substrate surface. For example, the isolating layer can be provided by oxidation.

In a variant of these embodiments or variants, the hole ends at the isolating layer which forms the first substrate surface. In particular, the hole can be a blind hole. In this way, the isolating layer isolates the output of the data conversion device from the optical fiber, but is still thin enough for the optical signal to pass through. Thus, the isolating layer can in particular be optically transparent. Further, an easy manufacturing method for arranging the optical fiber within the substrate hole can be provided in this way. In the corresponding method, providing the hole is ended or ends at the isolating layer which forms the first substrate surface. For example, the hole can be etched from the second substrate surface through the substrate base layer and ending at the isolating layer.

In a further embodiment or variant, the optical fiber is fixedly connected to the substrate. In this way, the optical fiber(s) can be permanently attached to the substrate and thus the sensor arrangement. Thus, the optical fiber can be permanently coupled to the output of the data conversion device. This provides a better optical coupling. A smaller device compared to, for example, a detachable connection or an air gap between the optical fiber and the optical output can be provided. In particular, an optically transparent adhesive can be used for fixedly connecting the optical fiber to the substrate. For example, the remaining space of the hole in between the substrate and the optical fiber can be filled with the optically transparent adhesive. In the corresponding method, coupling the optical fiber to the optical output comprises fixedly connecting the optical fiber to the substrate, in particular using an optically transparent adhesive.

In a further embodiment or variant, the sensor arrangement further comprises an electrical wire extending from the distal end to the proximal end of the instrument. In this way, the device can be powered (e.g. the electrical wire(s) can be used for power supply to the sensor arrangement) and/or additional functionality can be provided. For example, the electrical wire(s) can be used for low speed data transport (e.g. of control signals). In the corresponding method, manufacturing the sensor arrangement further comprise providing an electrical wire extending from the distal end to the proximal end of the instrument.

In a further embodiment or variant, the electrical wire is arranged through a through-hole in the substrate, the through-hole extending from the first substrate surface to the second substrate surface. In this way, a simultaneous connection of electrical wire(s) and optical fiber(s) to the substrate (e.g. silicon chip) can be provided. This is particularly easy to manufacture. In the corresponding method, manufacturing the sensor arrangement further comprises providing a through-hole in the substrate, the through-hole extending from the first substrate surface to the second substrate surface, and arranging the electrical wire through the through-hole. For example, the through-hole can be etched through the substrate.

In another embodiment or variant, the electrical wire is fixedly connected to the substrate. In this way, the electrical wire(s) can be permanently attached to the substrate and thus the sensor arrangement. For example, a solder connection can be used to fixedly connect the electrical wire to the substrate. In particular, both the optical fiber and the electrical wire can be fixedly connected to the substrate. In the corresponding method, manufacturing the sensor arrangement further comprises fixedly connecting the electrical wire to the substrate.

In a further embodiment or variant, the sensor is arranged on a second substrate which is located, in a length direction of the medical instrument, above or below the substrate on which the data conversion device is arranged. Thus, the sensor and the data conversion device are arranged on different or separate substrates. In this way, a small sized medical instrument can be provided. In the corresponding method, manufacturing the sensor arrangement further comprises providing a second substrate on which the sensor is arranged, and locating the second substrate, in a length direction of the medical instrument, above or below the substrate on which the data conversion device is arranged.

In a further embodiment or variant, the sensor arrangement comprises a pre-processing electronic circuit configured to pre-process the electrical sensor signal, the pre-processing electronic circuit comprising an input for receiving the electrical sensor signal and an output for transmitting the pre-processed electrical sensor signal to the data conversion device. In this way, the pre-processing can be done at the distal end or tip of the medical instrument. For example, the pre-processing can be conditioning the electrical signal for conversion by the data conversion device and/or transmission over the optical fiber. However, the pre-processing electronic circuit generally cannot provide high data compression. The pre-processing electronic circuit generally does not need a lot of space. Thus, it can be easily integrated in the sensor arrangement at the distal end of the medical instrument. In this way, not the raw sensor data or signal from the sensor needs to be transmitted to the proximal end, but the sensor data can be pre-processed. For example, the pre-processing electronic circuit can be configured to amplify and/or multiplex the electrical sensor signal (e.g. so that it can be transmitted over the optical fiber). In particular, the pre-processing electronic circuit can be the electronic circuit used to control the sensor, for example an Application-Specified Integrated Circuit (ASIC), or it can be integrated there into or be part there of. In the corresponding method, manufacturing the sensor arrangement further comprises providing such a pre-processing electronic circuit.

In another embodiment or variant, the pre-processing electronic circuit is arranged on a third substrate which is located, in a length direction of the medical instrument, above or below the substrate on which the data conversion device is arranged. Thus, the pre-processing electronic circuit and the data conversion device are arranged on different or separate substrates. In this way, a small sized medical instrument is provided. In the corresponding method, manufacturing the sensor arrangement further comprises providing a third substrate on which the pre-processing electronic circuit is arranged, and locating the third substrate, in a length direction of the medical instrument, above or below the substrate on which the data conversion device is arranged.

In a further embodiment or variant, the instrument is a guide wire having an elongated guide wire core. A guide wire is a particularly useful minimally invasive medical instrument.

In a variant of this embodiment, the optical fiber forms the guide wire core. In this way, the medical device is cheaper and/or the size of the medical instrument can be further reduced. The optical fiber is not only used for transmitting the sensor data to the proximal end, but also as the mechanical core or support of the guide wire.

In a further embodiment or variant, the data conversion device is a Vertical-Cavity Surface-Emitting Laser (VCSEL), a Light-Emitting Diode (LED) or a Dynamic Mirror Device (DMD). In this way, a cheap and/or small device can be provided. A VCSEL is particularly useful for transmitting the optical signal towards the first substrate surface.

In a further embodiment or variant, the data conversion device is further configured to convert an optical signal into an electrical signal. In this way, the data conversion device can convert the signals both ways. In this case, the optical fiber provides both a high-speed optical data link from and to the distal end. This enables two way communication. For example, the data conversion device can be a VCSEL having a photodiode (e.g. underneath or surrounding the VCSEL). For example, the electrical signal can be used to drive and/or control the sensor.

BRIEF DESCRIPTION OF THE DRAWINGS

These and other aspects of the invention will be apparent from and elucidated with reference to the embodiment(s) described hereinafter. In the following drawings

FIG. 4a-4d show a method of manufacturing the sensor arrangement of FIG. 3;

FIG. 6 shows a schematic cross-section of a medical instrument according to another embodiment.

DETAILED DESCRIPTION OF THE INVENTION

Figure 1:
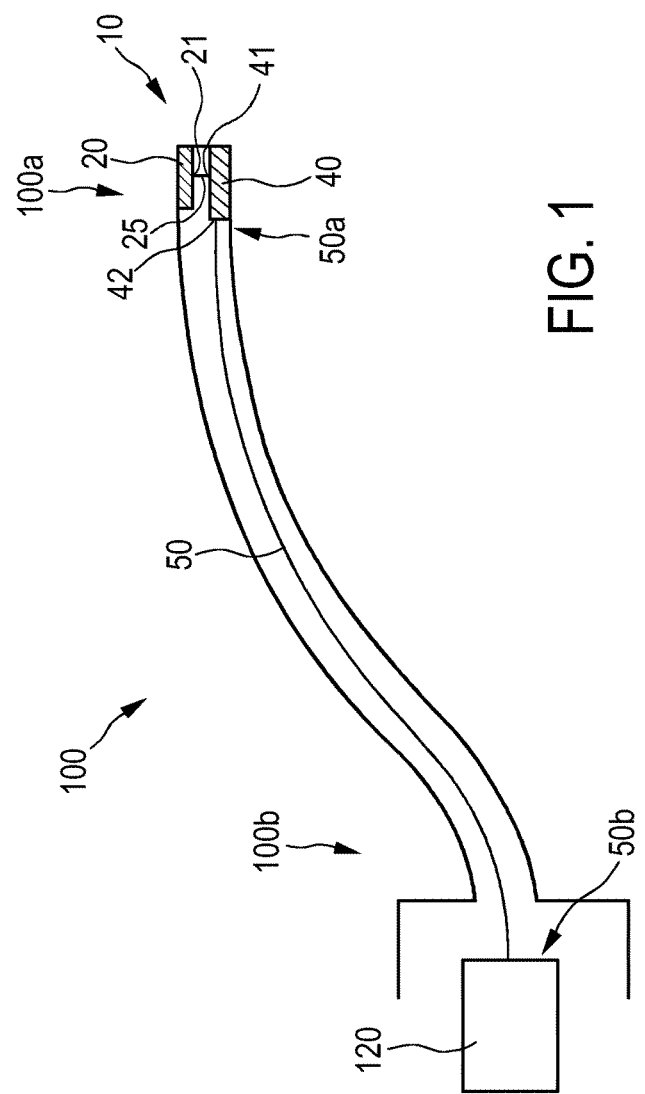
FIG. 1 shows a schematic diagram of a minimally invasive medical instrument according to an embodiment.

FIG. 1 shows a schematic diagram of a minimally invasive medical instrument 100 according to an embodiment. The minimally invasive medical instrument 100 (or also called minimally invasive medical device) has a proximal end 100b and a distal end 100a (or also called distal tip). In a medical invasive intervention, the distal end 100a is placed at an anatomical site in the body of a patient wherein the intervention is to be made. The minimally invasive medical instrument 100 comprises a sensor arrangement 10 arranged at the distal end 100a of the medical instrument. The sensor arrangement 10 comprises a sensor 20 configured to generate sensor data in the form of an electrical sensor signal. The sensor 20 comprises a sensor output 21 for transmitting the electrical sensor signal. The sensor arrangement further comprises a data conversion device 40 configured to convert the electrical sensor signal into an optical signal. The data conversion device 40 comprises an electrical input 41 for receiving the electrical sensor signal from the sensor 20, more particularly from the sensor output 21. The sensor output 21 is connected to the electrical input 41 of the data conversion device 40 via an electrical connection 25. The data conversion device 40 further comprises an optical output 42 for transmitting the optical signal. The sensor arrangement 10 further comprises an optical fiber 50 configured to transmit the optical signal from the distal end 100a to the proximal end 100b, in particular an optical glass fiber. For example, the length of the optical fiber 50 is long enough to reach from the distal end 100a to the proximal end 100b. The optical fiber 100 has a first end 50a and a second end 50b. The optical fiber 50 is coupled to the optical output 42 of the data conversion device 40 for receiving the optical signal. More particularly, the first end 50a of the optical fiber 50 is coupled to the output 42 of the data conversion device 40. The optical fiber 50 extends from the distal end 100a to the proximal end 100b of the medical instrument 100. The second end 50b of the optical fiber 50 is arranged at the proximal end 100b of the medical instrument 100. Thus, the optical fiber is used for transmitting the high-data-rate sensor data of the sensor 20 from the distal end 100a to the proximal end 100b of the medical instrument 100. This provides a high-speed optical data link from and/or to the distal end 100a of the medical instrument 100. Even though only one optical fiber 50 is shown in the drawings, it will be understood that any number or a plurality of optical fibers can be used.

In the embodiment shown in FIG. 1, the second end 50b of the optical fiber 50 is connected to a signal processing device 120 configured to read out and/or process the sensor data or electrical sensor signal, for example for medical imaging. For example, the signal processing device 120 can be configured to convert the optical signal (received from the optical fiber 50) back into an electrical signal. Also, the signal processing device 120 can be configured to process the electrical signal in the digital domain (e.g. as required by the application).

The corresponding method for manufacturing such a minimally invasive medical instrument 100 first comprises manufacturing such a sensor arrangement 10. Manufacturing the sensor arrangement 10 comprises providing the sensor 20, providing the data conversion device 40, providing the optical fiber 50, and coupling the optical fiber 50 to the output 42 of the data conversion device 40. The method for manufacturing the medical instrument 100 further comprises arranging the sensor arrangement 10 at the distal end of the medical instrument 100. The optical fiber 50 then extends from the distal end 100a to the proximal end 100b of the instrument 100.

In this description, the sensor 20 shown in the Figures is an ultrasound transducer configured to transmit and/or receive ultrasound waves, in particular a capacitive micromachined ultrasound transducer (CMUT). This is a particularly useful sensor for a minimally invasive device, in particular for medical imaging. An ultrasound transducer generates a high amount of sensor data, thus a high data rate, which requires a high data rate transmission. In particular, the ultrasound transducer 20 can comprise a plurality of ultrasound transducer cells 22, in particular CMUT cells, arranged next to one another. However, it will be understood that the sensor can be any other kind of medical imaging sensor which generates sensor data representing an image (e.g. of the patient's body or part thereof). For example, the sensor can be a camera (e.g. CCD chip or CMOS image sensor chip). Medical imaging sensors generate a high amount of sensor data, thus a high data rate, which requires a high data rate transmission. However, it will be understood that in general any other type of sensor can be used, in particular a sensor generating a high data rate. In general, the sensor can also be a sensor generating a low data rate, such as a pressure sensor. However, the high-speed optical data link described herein is particularly useful for a sensor generating a high data rate, such as an ultrasound transducer or camera.

Figure 2:
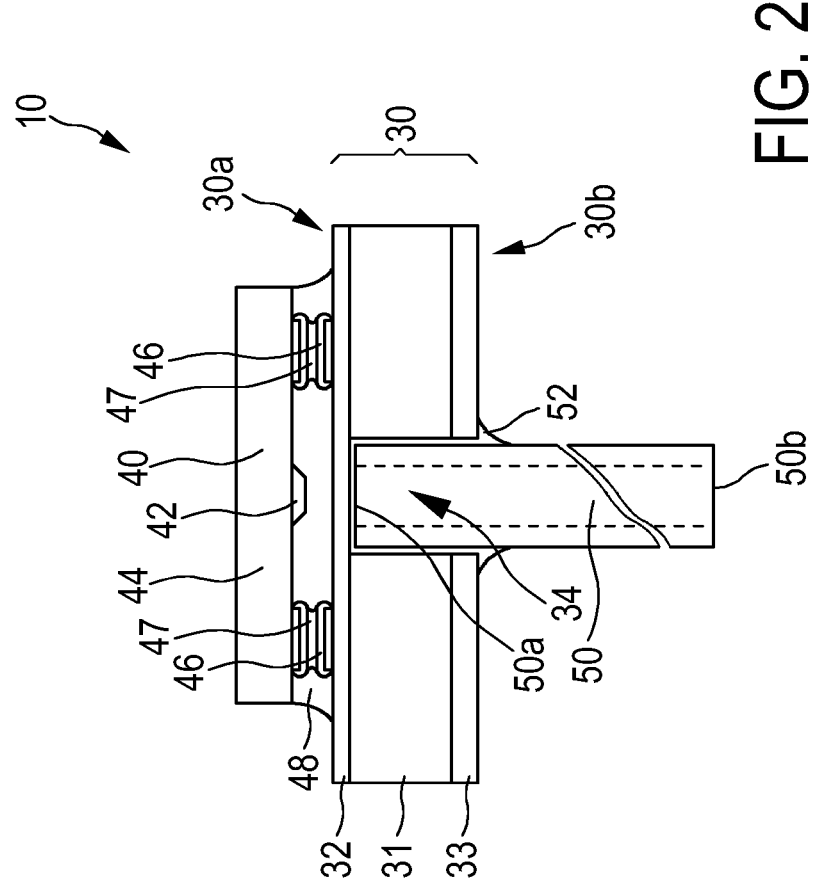
FIG. 2 shows a schematic cross-section of part of a sensor arrangement of the medical instrument according to an embodiment.

FIG. 2 shows a schematic cross-section of part of a sensor arrangement 100 of the medical instrument 100 according to an embodiment, in particular the medical instrument as explained with reference to FIG. 1. The sensor arrangement 10 comprises a sensor (not shown in FIG. 2), a data conversion device 40, and an optical fiber 50, in particular as explained with reference to FIG. 1. The sensor arrangement 10 further comprises a substrate 30 (e.g. silicon chip) having a first surface 30a and a second surface 30b. The data conversion device 40 is arranged on or attached to the first substrate surface 30a. In this embodiment shown in FIG. 2, the optical fiber 50 is arranged in a hole 34 in the substrate 30. The hole 34 extends from the second substrate surface 30b towards the first substrate surface 30a. The hole 34 is arranged perpendicular to the substrate surfaces 30a, 30b. Thus, also the optical fiber 50 arranged in the hole 34 is arranged perpendicular to the substrate surfaces 30a, 30b. The hole 34 is arranged such that the first end 50a of the optical fiber 50 is coupled to the output 42 of the data conversion device 40. In other words, the data conversion device 40 is arranged to transmit the optical signal towards the first substrate surface 30a in a region where the first end 50a of the optical fiber 50 is located. The first end 50a or hole 34 is placed centered around the optical output 42 so that the center of the optical fiber 50 receives the entire optical signal or light transmitted from the optical output. The second end 50b of the optical fiber is arranged at the proximal end 100 b of the medical instrument. In order to illustrate this, the optical fiber is shown with a cut through in FIG. 2.

In this embodiment shown in FIG. 2, the substrate has a base layer 31 (e.g. made of silicon) and a first isolating layer 32 (e.g. an oxide, such as silicon oxide) on the base layer 31, the first isolating layer 32 forming first substrate surface 30a. The isolating layer 32 electrically isolates or insulates. By using this first isolating layer 32, electrical connection parts 46 for providing an electrical connection to the data conversion device 40 can be arranged on the first substrate 30a, even if the base layer 31 is conductive or semi-conductive. For example, the base layer 30 can be made of silicon. In this case the isolating layer can be made of silicon oxide which can be formed by oxidizing the silicon. Optionally, the substrate 30 may have a second isolating layer 33 on the base layer 31, the second isolating layer 33 forming the second substrate surface 30b, as shown in FIG. 2.

In this embodiment shown in FIG. 2, the hole 34 ends at the first isolating layer 32 which forms the first substrate surface 30a. Thus, the hole 34 is a blind hole. The first isolating layer 32 is optically transparent. For example, silicon oxide is optically transparent. The first isolating layer 32 isolates the optical output 42 of the data conversion device 40 from the optical fiber 50, but is still thin enough for the optical signal to pass through the isolating layer 32. The optical fiber 50 is fixedly connected to the substrate 30. In other words, the optical fiber 50 is permanently attached to the substrate 30. Thus, the optical fiber 50 is permanently coupled to the output 42 of the data conversion device 40. In particular, an optically transparent adhesive 52 is used for fixedly connecting the optical fiber 50 to the substrate 30. As can be seen in FIG. 2, the remaining space of the hole 34, in particular the space between the substrate 30 (or its isolating layer 32) and the optical fiber 50, is filled with the optically transparent adhesive 52. This improves optical coupling. Further, as can be seen in FIG. 2, an optically transparent under fill 48 is arranged between the data conversion device 40 and the first substrate surface 30a, more particularly between the optical output 42 of the data conversion device 40 and the first substrate surface 30a (or first end 50a of the optical fiber 50). This improves optical coupling even further.

In this description, the data conversion device 40 shown in the Figures is a Vertical-Cavity Surface-Emitting Laser (VCSEL). The VCSEL 40 has an electrical input for receiving the electrical sensor signal. In FIG. 2, the electrical connection parts 46 for providing an electrical connection to the data conversion device 40, in particular from the sensor 20, are connected to the VCSEL 40 or its input by solder bumps 47. The VCSEL 40 comprises an active region 44 for generating laser light. In particular, the active region 44 comprises a first mirror (or Bragg reflector), a second mirror (or Bragg reflector), and a laser cavity (or quantum well(s)) arranged in between the first and second mirror. The VCSEL 40 further comprises an optical output 42. The optical output 42 faces the first substrate surface 30a. The optical output 42 receives the generated laser light and transmits or emits it as the optical signal. The VCSEL 40 is particularly useful for transmitting the optical signal towards the first substrate surface 30a. However, it will be understood that in general any other type of data conversion device configured to convert the electrical sensor signal into an optical signal can be used. For example, the data conversion device can be a Light-Emitting Diode (LED) or a Dynamic Mirror Device (DMD).

The data conversion device 40 can further be configured to convert an optical signal (transmitted via the optical fiber 50) into an electrical signal (e.g. to drive and/or control the sensor). In this way, the data conversion device 40 can convert the signals both ways. Thus, the optical fiber 50 provides a high-speed optical data link both from the distal end 100a as well as to the distal end 100a. This enables two way communication. If the data conversion device is a VCSEL, as explained above, for example a photodiode can be arranged underneath or surrounding the VCSEL or its active region.

Figure 3:
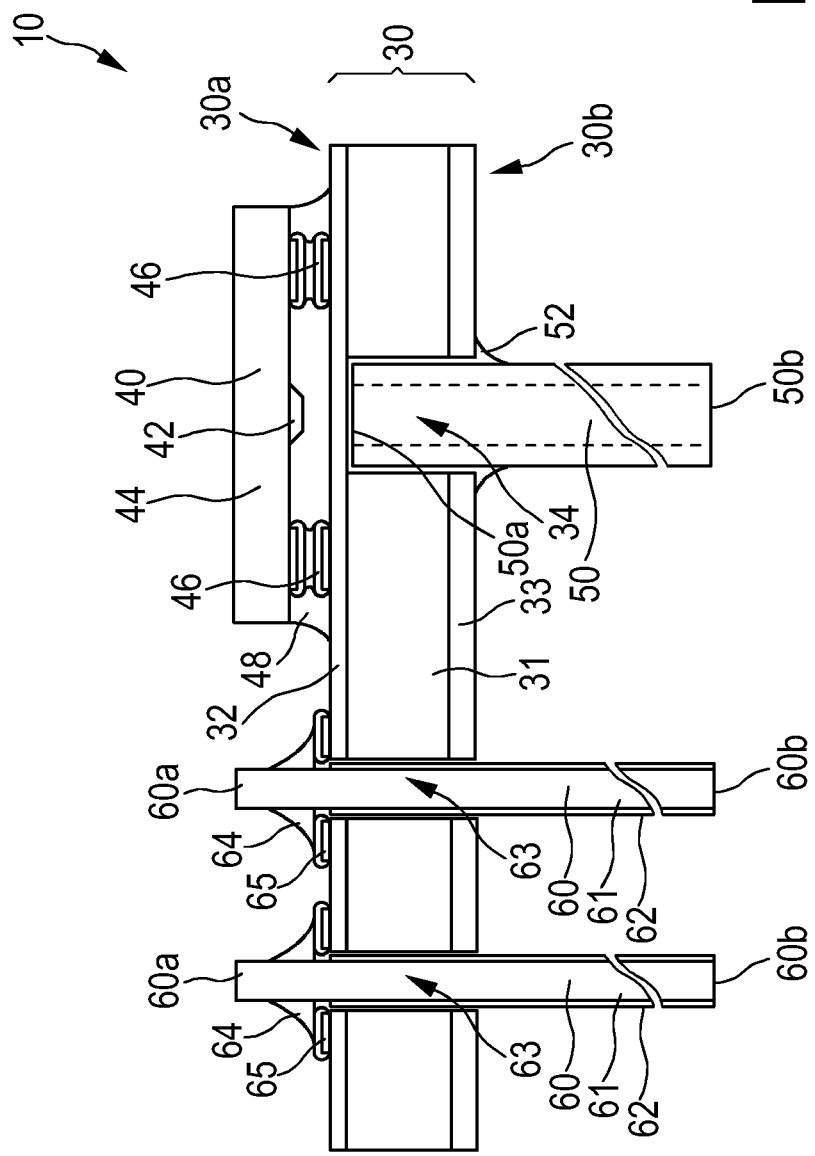
FIG. 3 shows a schematic cross-section of part of a sensor arrangement of the medical instrument according to another embodiment.

FIG. 3 shows a schematic cross-section of part of a sensor arrangement 10 of the medical instrument 100 according to another embodiment. As the embodiment of FIG. 3 is based on the embodiment of FIG. 2, the same explanations made for the embodiment of FIG. 2 also apply to the embodiment of FIG. 3. In the embodiment shown in FIG. 3, the sensor arrangement 10 additionally comprises an electrical wire 60 extending from the distal end 100a to the proximal end 100b of the medical instrument 100. The electrical wire 60 comprises a first end 60a and a second end 60b. The first end 60a is arranged at the sensor arrangement 10, thus at the distal end 100a of the medical instrument. The second end 60b is arranged at the proximal end 100b of the medical instrument. In order to illustrate this, the electrical wire is shown with a cut through in FIG. 3. In the embodiment of FIG. 3, two electrical wires 60 arranged next to each other are shown. However, it will be understood that any other (suitable) number of electrical wires can be used. For example, the electrical wire(s) 60 can be used for power supply to the sensor arrangement or for low speed data transport (e.g. of control signals).

The electrical wire 60 is arranged through a through-hole 63 in the substrate 30, the through-hole 63 extending from the first substrate surface 30a to the second substrate surface 30b, or the other way round. By providing the hole 34 for the optical fiber 50 and the through-hole 63 for the electrical wire 60, a simultaneous connection of the optical fiber 50 and the electrical wire 60 to the substrate 30 can be provided in an easy manner, for example in one processing step (e.g. etching). The electrical wire 60 comprises a conductive core 61 and an isolation 62 surrounding the core 61. The isolation 62 electrically isolates or insulates the conductive core 61. As can be seen in FIG. 3, the electrical wire 60 or core 61 is fixedly connected to the substrate 30. In other words, the electrical wire 60 is permanently attached to the substrate 30. At the first end 60b the electrical wire 60 has an isolation-free portion. For example, as can be seen in FIG. 3, a solder joint 64 can be used to fixedly connect the electrical wire 60 or core 61 at the first end 60a to the substrate 30. As can be seen in FIG. 3, the core 61 of the electrical wire 60 at its first end 60a is connected by solder joint 64 to an electrical connection part 65 on the first substrate surface 30a. In summary, in the embodiment of FIG. 3, both the optical fiber 50 and the electrical wire 60 are fixedly connected to the substrate. The optical fiber 50 is fixedly connected by an optically transparent adhesive 52 and the electrical wire 60 is fixedly connected by a solder joint or connection.

Figure 4C:
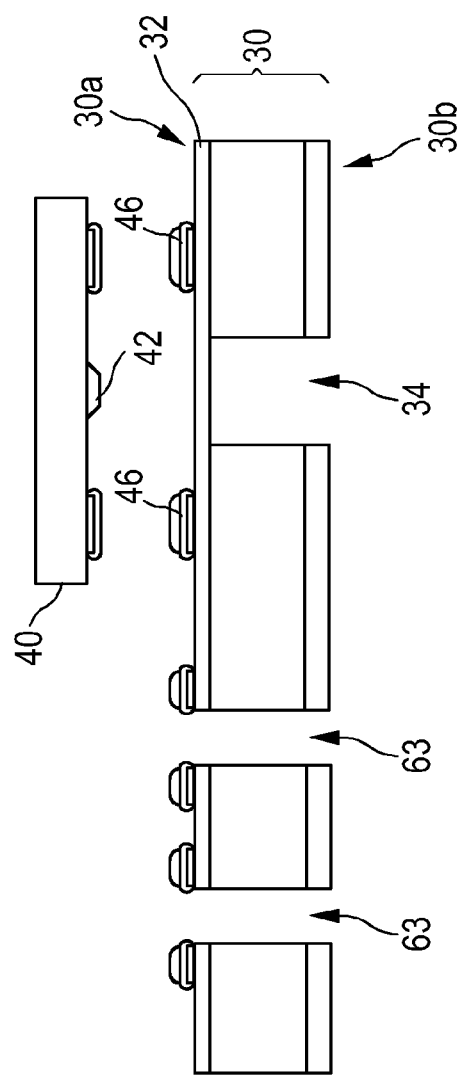

Now, the method of manufacturing the sensor arrangement 10 will be explained in more detail with reference to FIG. 4a-4d. Each of FIG. 4a-4d shows a different step of a method of manufacturing the sensor arrangement 10 of FIG. 3. The manufacturing of the sensor arrangement 10 starts with providing the substrate 30 (e.g. silicon chip) having the first surface 30a and a second surface 30b. For example, as shown in FIG. 4a, a base layer 31 (e.g. made of silicon) can be provided and then an isolating layer 32 (e.g. made of oxide, such as silicon oxide) can be provided on the base layer 31 (e.g. by thermal oxidization). The isolating layer 32 now forms the first substrate surface 30a. Then, the sensor 20 may be provided on the first substrate surface 30a, more particularly the isolating layer 32 (not shown in FIG. 4a). Subsequently, now referring to FIG. 4b, a hole 34 is provided in the substrate 30 (e.g. by etching), the hole 34 extending from the second substrate surface 30b towards the first substrate surface 30a. As can be seen in FIG. 4b, providing the hole 34 is ended at the isolating layer 32. In this case, the hole 34 is etched from the second substrate surface 30b through the substrate base layer 31 and ending at the isolating layer 32. As indicated in FIG. 4b, further a through-hole 63 is provided in the substrate 30, the through-hole 63 extending from the second substrate surface 30b all the way through to the first substrate surface 30a. In this case, the through-hole 63 is etched from the second substrate surface 30b all the way through the substrate 30. In particular, providing (e.g. etching) the hole 34 and providing (e.g. etching) the through-hole 63 are performed in one single processing step. Optionally, as shown in FIG. 4b, a support layer 49 (e.g. made of polyimide) may be used when providing (e.g. etching) the hole 34 and the through-hole 63.

Figure 4D:
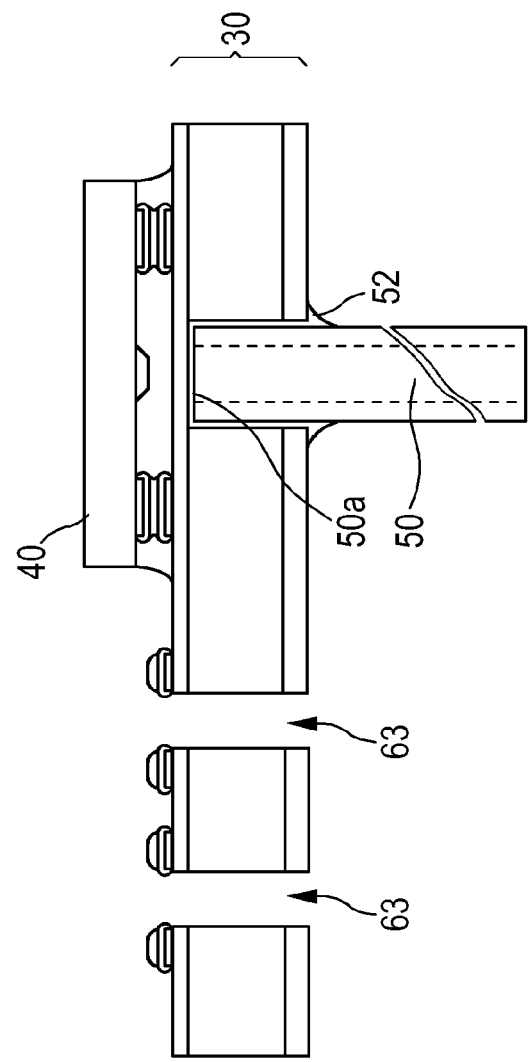

Then, referring to FIG. 4c, the data conversion device 40 is provided. The data conversion device 40 is arranged on the first substrate surface 30a. In this case, electrical connection to the electrical connection parts 46 arranged on the first substrate surface 30a is made. Now, as can be seen in FIG. 4d, the optical fiber 50 is provided. The optical fiber 50 (or its first end 50a) is coupled to the optical output 42 of the data conversion device 40. This is done by arranging the optical fiber 50 in the hole 34. Then, for fixedly connecting the optical fiber 50 to the substrate 30, the optically transparent adhesive 52 is filled in the remaining space of the hole 34. Finally, the electrical wire 60 (see FIG. 3) is provided. The electrical wire 60 is arranged through the through-hole 63. For fixedly connecting the electrical wire 60 to the substrate 30, a solder joint 64 can be used. It will be understood that the steps described above can also be performed in any other suitable sequence.

Figure 5:
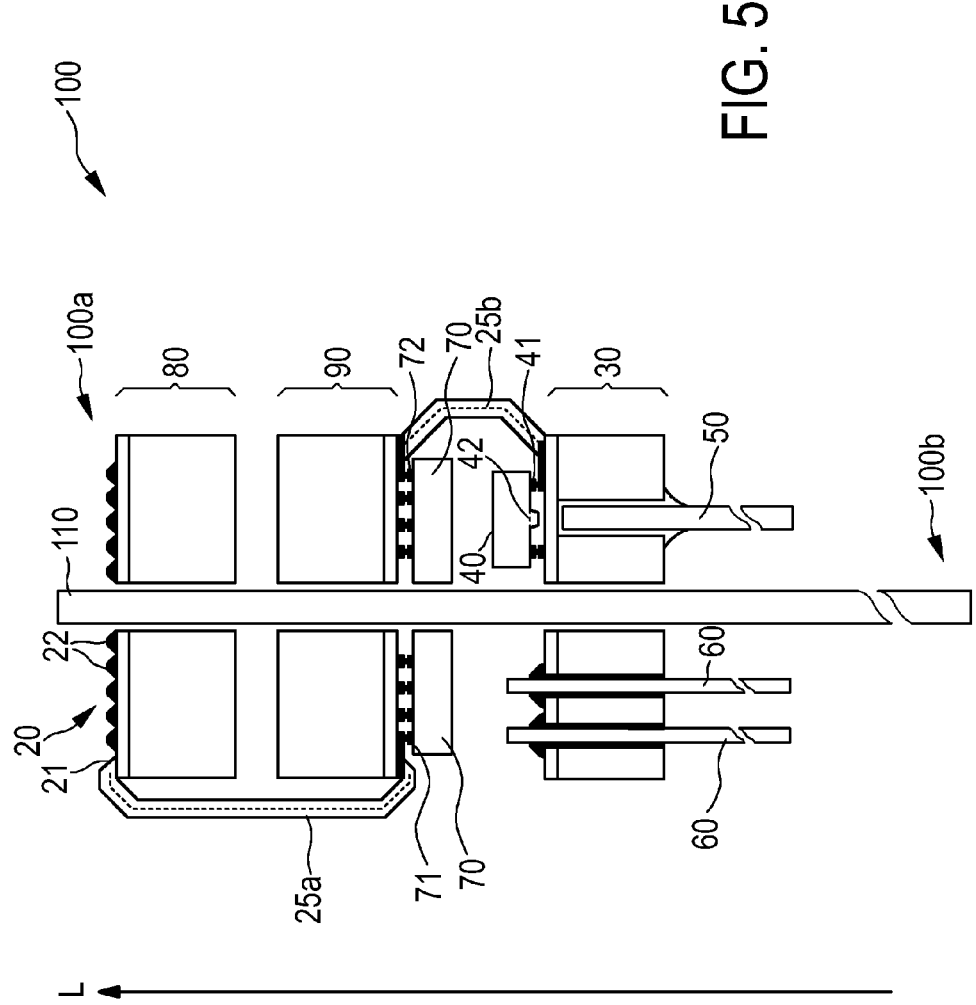
FIG. 5 shows a schematic cross-section of a medical instrument according to an embodiment.
Figure 5A:
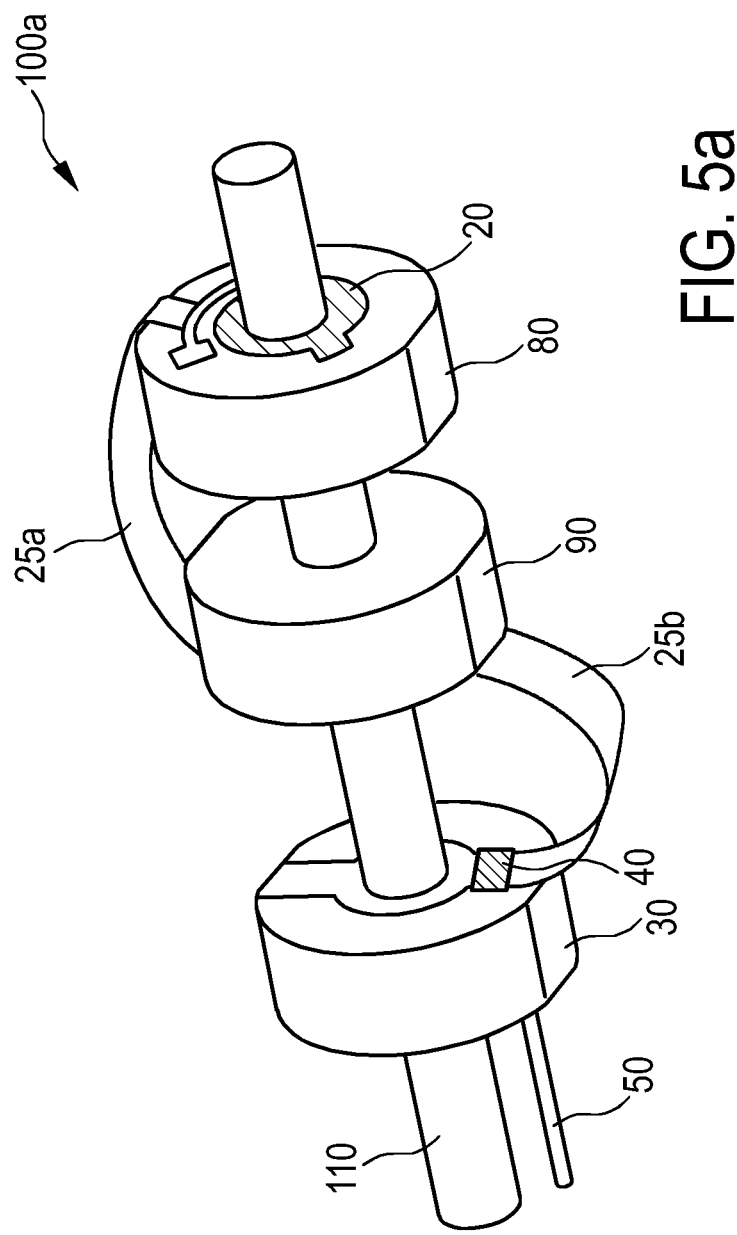
FIG. 5a shows a perspective view of the distal end of the medical instrument of FIG. 5.

FIG. 5 shows a schematic cross-section of a medical instrument 100 according to an embodiment, and FIG. 5a shows a perspective view of the distal end 100a of the medical instrument 100 of FIG. 5. The part of the sensor arrangement 10 as described with reference to FIG. 3 is used in this embodiment. Thus, the explanations to the previous embodiments also apply to the embodiment of FIG. 5. In the embodiment shown in FIG. 5, the sensor arrangement 10 further comprises a pre-processing electronic circuit 70 configured to pre-process the electrical sensor signal. Thus, the pre-processing is done at the distal end 100a of the medical instrument 100. For example, the pre-processing electronic circuit 70 can be configured to amplify and/or multiplex the electrical sensor signal. In this way, not the raw sensor data or signal from the sensor 20 needs to be transmitted to the proximal end 100b, but the sensor data can be pre-processed (e.g. conditioned). The pre-processing electronic circuit can in particular be the electronic circuit used to control the sensor 20, or it can be or be integrated there into or be part there of. For example, it can be an Application-Specified Integrated Circuit (ASIC). The pre-processing electronic circuit 70 comprises an input 71 for receiving the electrical sensor signal from the sensor 20. In particular, the pre-processing electronic circuit can comprises a plurality of input ports for receiving the electrical sensor signals from the sensor. An electrical connection 25a is provided between the sensor 20 or sensor output 21 and the electronic circuit 70 or its input 71. The pre-processing electronic circuit 70 further comprises an output 72 for transmitting the pre-processed electrical sensor signal to the data conversion device 40. An electrical connection 25b is provided between the electronic circuit 70 or its output 72 and the data conversion device 40 or its input 41. In the embodiment of FIG. 5 (see also FIG. 5a), the electrical connections 25a, 25b are flexible electrical connections. It will be understood that the pre-processing electronic circuit 70 can also be used in connection with any of the embodiments described above with reference to FIG. 1 to FIG. 4.

Further, in the embodiment of FIG. 5, the sensor 20 (in this case the ultrasound transducer cells 22) is arranged on a second substrate 80 which is located, in the length direction L of the medical instrument 100 (which in this case is defined in a direction from the proximal end 100b to the distal end 100a), above the first substrate 30 on which the data conversion device 40 is arranged. Thus, the sensor 20 and the data conversion device 40 are arranged on two separate substrates 30, 80. Furthermore, the pre-processing electronic circuit 70 is arranged on a third substrate 90 which is located, in the length direction L, above the first substrate 30 on which the data conversion device 40 is arranged. Thus, also the pre-processing electronic circuit 70 and the data conversion device 40 are arranged on two separate substrates 30, 90. In other words, each of the data conversion device 40, the sensor 20 and the pre-processing electronic circuit 70 is arranged on a separate substrate. In the embodiment of FIG. 5, the third substrate 90 is located below the second substrate 80, thus between the first substrate 30 and the second substrate 80. The second substrate 80 with the sensor 20 is arranged at the distal most part of the instrument 100 in order to sense, or generate the sensor data, in an optimal way.

In the embodiment of FIG. 5, the medical instrument 100 is a guide wire having an elongated guide wire core 110 (e.g. made of stainless steel). Each of the first substrate 30, the second substrate 80, and the third substrate 90 is a disk surrounding the guide wire core 110, as can be seen in FIG. 5a. The guide wire may also comprise a retractable sheath surrounding the guide wire (e.g. surrounding the substrates 30, 80, 90). However, it will be understood that in general any other suitable minimally invasive medical instrument can be used.

Figure 5B:
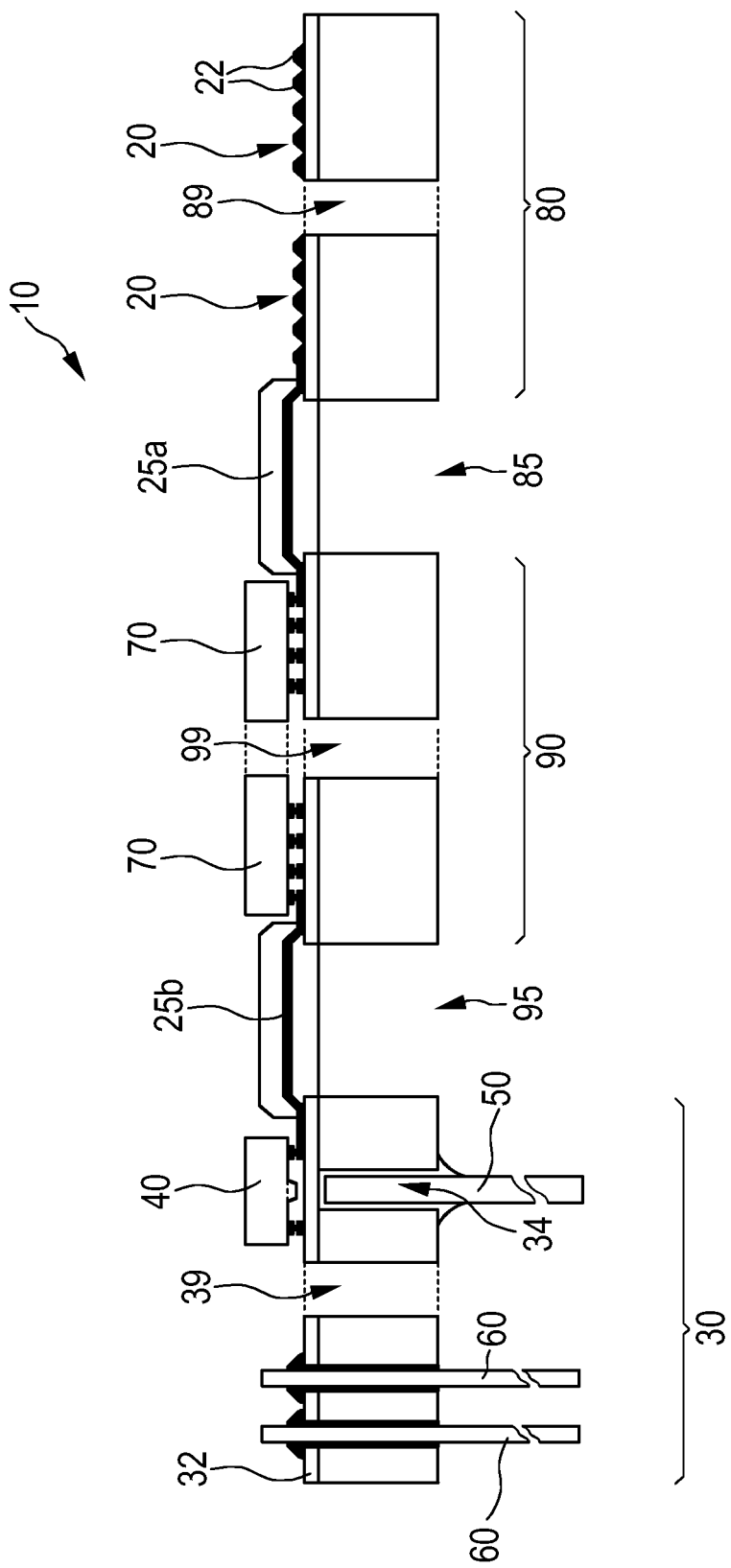
FIG. 5b shows a schematic cross-section of the sensor arrangement of FIG. 5 at the end of its manufacturing.

FIG. 5b shows a schematic cross-section of the sensor arrangement 10 of FIG. 5 at the end of its manufacturing. The corresponding manufacturing method comprises providing the first substrate 30 on which the data conversion device 40 is arranged, providing the second substrate 80 on which the sensor 20 is arranged, and providing the third substrate 90 on which the pre-processing electronic circuit 70 is arranged. In the embodiment of FIG. 5b, the first substrate 30, the second substrate 80 and the third substrate 90 are formed from one single continuous substrate. The substrates 30, 80, 90 are separated from each other by etching separation holes 85, 95 in the single continuous substrate. In this way, the sensor arrangement 10 with the substrates 30, 80, 90 can be manufactured in an easy manner.

After the sensor arrangement 10 has been manufactured as shown in FIG. 5b, the second substrate 80 and the third substrate 90 are each located, in the length direction L, above the first substrate 30 (see FIG. 5 or FIG. 5a). The flexible electrical connections 25a, 25b provide electrical connection between the sensor 20, the electronic circuit 70, and the data conversion device 40 on the different substrates 30, 80, 90.

FIG. 6 shows a schematic cross-section of a medical instrument 100 according to another embodiment. The embodiment of FIG. 6 differs from the embodiment of FIG. 5 in that the optical fiber 50 now forms the guide wire core 110. The guide wire core 110 of FIG. 5 is replaced by the optical fiber 50. Thus, the optical fiber 50 is not only used for transmitting the sensor data of the sensor 20 (not shown in FIG. 6) to the proximal end, but also as the mechanical core 110 or support of the guide wire. For example, in the embodiment of FIG. 6, the sensor 20 may be placed around the substrate or substrates, in particular bent around the circumference of the guide wire.

Further, the embodiment of FIG. 6 differs from the embodiment of FIG. 5 in that the third substrate 90 with the electronic circuit 70 is located, in the length direction L, below the first substrate 30 with the data conversion device 40. The first substrate 30 with the optical fiber 50 connected thereto is arranged at the distal most part of the instrument 100 in order to provide mechanical support all the way through to the distal most part of the medical instrument 100.

Figure 7:
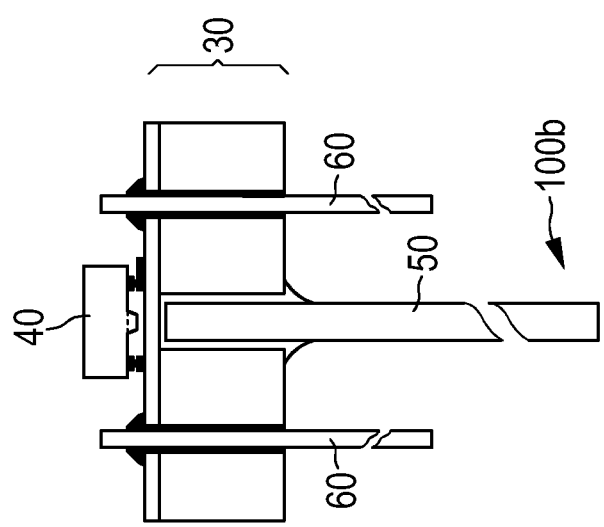
FIG. 7 shows a schematic cross-section of part of a medical instrument according to yet another embodiment.

Furthermore, the embodiment of FIG. 6 differs from the embodiment of FIG. 5 in that the electrical wire(s) 60 is arranged on an additional substrate 92. Thus, the data conversion device 40 and the electrical wire(s) 60 are arranged on two separate substrates. The additional substrate 92 is located, in the length direction L, below the first substrate 30 and also below the third substrate 90. However, it will be understood that the electrical wire 60 can also be arranged in any other suitable way. For example, FIG. 7 shows a schematic cross-section of part of a medical instrument according to yet another embodiment. In this embodiment of FIG. 7, the electrical wire 60 is arranged on the same substrate 30 as the data conversion device 40.

Even though a guide wire has been described herein, it will be understood that the minimally invasive medical instrument can be any type of minimally invasive medical instrument. For example, the minimally invasive medical instrument can be a catheter, guide wire, laparoscopic instrument or endoscope. A minimally invasive medical instrument can for example have a diameter of 10000 µm or less, in particular 8000 µm or less, in particular 3000 µm or less, in particular 1000 µm or less, in particular 500 µm or less, in particular 300 µm or less. Just as a specific example, a laparoscopic instrument can for example have a diameter between 8 mm to 3 mm, a catheter can have a diameter between 3 mm to 1 mm, and/or a guide wire can have a diameter of less than 0.5 mm. For example, the minimally invasive medical instrument can be a smart medical instrument. A smart medical instrument comprises a sensor and sensor electronics (e.g. ASIC) at its distal end.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A minimally invasive medical instrument, comprising:
    a guide wire comprising a proximal end, a distal end, and a guide wire core;
    a sensor arrangement disposed at the distal end of the guide wire, the sensor arrangement comprising:
        a sensor configured to generate sensor data in the form of an electrical sensor signal;
        a data conversion device configured to convert the electrical sensor signal into an optical signal and comprising an electrical input for receiving the electrical sensor signal and an optical output for transmitting the optical signal;
        an electronic circuit configured to pre-process the electrical sensor signal received from the sensor and transmit the pre-processed electrical sensor signal to the data conversion device, the electronic circuit being arranged on a first substrate comprising a first through hole; and
        an optical fiber configured to transmit the optical signal from the distal end to the proximal end, the optical fiber coupled to the output of the data conversion device for receiving the optical signal, the optical fiber extending from the distal end to the proximal end of the instrument,
    wherein the guide wire core extends completely through the first through hole.

2. The medical instrument of claim 1, wherein the sensor arrangement further comprises a second substrate comprising a first surface and a second surface, the data conversion device arranged on the first surface of the second substrate.

3. The medical instrument of claim 2, wherein the optical fiber is arranged in a hole in the second substrate, the hole extending from the second surface towards the first surface of the second substrate.

4. The medical instrument of claim 3, wherein the second substrate comprises a base layer, in particular made of silicon, and at least one isolating layer on the base layer, in particular made of silicon oxide, the isolating layer forming at least the first substrate surface.

5. The medical instrument of claims 4, wherein the hole ends at the isolating layer which forms the first surface.

6. The medical instrument of claim 2, wherein the optical fiber is fixedly connected to the second substrate.

7. The medical instrument of claim 1, wherein the sensor arrangement further comprises an electrical wire extending from the distal end to the proximal end of the instrument.

8. The medical instrument of claim 1, wherein the data conversion device is a Vertical-Cavity Surface-Emitting Laser (VCSEL), a Light-Emitting Diode (LED) or a Dynamic Mirror Device (DMD).

9. The medical instrument of claim 1, wherein the data conversion device is further configured to convert an optical signal into an electrical signal.

10. The medical instrument of claim 2, wherein the sensor is arranged on a third substrate which is located, in a length direction (L) of the medical instrument, above or below the second substrate on which the data conversion device is arranged.

11. The medical instrument of claim 10, wherein the first substrate is located, in a length direction (L) of the medical instrument, above or below the second.

12. The medical instrument of claim 10, wherein each of the first, second, and third substrates are disk-shaped.

13. The medical instrument of claim 12, wherein the guide wire core is the optical fiber.

14. The medical instrument of claim 12, wherein the second substrate comprises a second through hole along a direction normal to a surface of the second substrate, the third substrate comprises a third through hole along a direction normal to a surface of the third substrate, and wherein the guide wire core extends completely through the second and third through holes.

15. A method for manufacturing a minimally invasive medical instrument having a proximal end and a distal end, the method comprising:
    manufacturing a sensor arrangement comprising:
        providing a sensor configured to generate sensor data in the form of an electrical sensor signal, the sensor being arranged on a first substrate;
        providing a data conversion device configured to convert the electrical sensor signal into an optical signal and comprising an electrical input for receiving the electric sensor signal and an optical output for transmitting the optical signal, the data conversion device being arranged on a second substrate;
        providing an electronic circuit configured to pre-process the electrical sensor signal, the electronic circuit comprising an input for receiving the electrical sensor signal and an output for transmitting the pre-processed electrical sensor signal to the data conversion device, the electronic circuit being arranged on a third substrate, the third substrate comprising a through hole;
        providing a guide wire core;
        threading the guide wire core completely through the through hole; and
        arranging the first, second, and third substrates in a length direction,
    the method further comprising:
    arranging the sensor arrangement at the distal end of the medical instrument.

* * * * *